(12) United States Patent
Zech et al.

(10) Patent No.: US 6,335,413 B1
(45) Date of Patent: Jan. 1, 2002

(54) HARDENABLE MASS WITH SILANE DENDRIMERS

(75) Inventors: Joachim Zech, Seefeld; Gunther Lechner, Worthsee, both of (DE)

(73) Assignee: ESPE Dental AG, Seefeld (DE)

( * ) Notice: Subject to any disclaimer, the term of this patent is extended or adjusted under 35 U.S.C. 154(b) by 0 days.

(21) Appl. No.: 09/485,069

(22) PCT Filed: Aug. 21, 1998

(86) PCT No.: PCT/EP98/05319

§ 371 Date: Feb. 3, 2000

§ 102(e) Date: Feb. 3, 2000

(87) PCT Pub. No.: WO99/09934

PCT Pub. Date: Mar. 4, 1999

(30) Foreign Application Priority Data

Aug. 22, 1997 (DE) .......................................... 197 36 665

(51) Int. Cl.[7] .............................................. C08G 77/20
(52) U.S. Cl. ................................. 528/32; 424/DIG. 16; 525/477; 525/478; 528/15; 528/31
(58) Field of Search ................... 424/DIG. 16; 525/477, 525/478; 528/15, 31, 32, 34

(56) References Cited

U.S. PATENT DOCUMENTS 5,276,110 A   1/1994  Zhou et al.
6,184,407 B1 * 2/2001  Yoshitake et al.

FOREIGN PATENT DOCUMENTS

DE  A1 1-9517838  11/1996
EP  A1 0614655    9/1994
EP  A2 0716103    6/1996
EP  A2 0743313    11/1996
WO  WO 96 12754  5/1996
WO  WO 96 32088  10/1996

OTHER PUBLICATIONS

"Preparation of Organosilane Dendrimer containing Allyl End Groups", Bull. Korean Chem. Soc., Kim et al., 1996, 17(5), 419 (abstract).*
"Preparation of Silane Dendrimer II", J. Korean. Chem. Soc., Kim et al., 1995, 39(10), 799 (abstract).*
"Silane Dendrimers", Van der Made et al., J. Chem. Soc., Chem. Comm., 1992, 1400 (abstract).*
Polymer Science, Series A, vol. 39, No. 8, 1997, pp. 875–881.
Chemical Abstract, vol. 122, Ref. 56637.

* cited by examiner

*Primary Examiner*—Robert Dawson
*Assistant Examiner*—Marc Zimmer
(74) *Attorney, Agent, or Firm*—Birch, Stewart, Kolasch & Birch, LLP

(57) ABSTRACT

The invention relates to curable materials containing
(A) optionally organopolysiloxanes with at least two unsaturated groups in the molecule,
(B) organohydrogenpolysiloxanes with at least 3 SiH groups in molecule,
(C) optionally organopolysiloxanes without reactive groups
(D) catalyst
(E) optionally hydrophilizing agents,
(F) fillers and
(G) optionally conventional dental additives, adjuvants and colorants, and
(H) at least one silane dendrimer with terminal alkenyl groups The materials are particularly suitable for dental materials and are characterized by a particularly good end hardness with excellent processing viscosity.

15 Claims, No Drawings

HARDENABLE MASS WITH SILANE DENDRIMERS

This application is the national phase under 35 U.S.C. §371 of PCT International Application No. PCT/EP98/05319 which has an International filing date of Aug. 21, 1998, which designated the United States of America.

The invention relates to curable compositions which contain highly-branched molecules on a silane base and are particularly suitable as dental materials.

For dental materials, there is a high demand for materials with high end hardness for the most varied indications. Materials for bite registration, temporary and permanent filling materials, crown and bridge materials as well as cement and enamel can be named as examples. The end hardness plays an important role in all of these uses, for example it determines the dimensional stability, cuttability and castability of impression materials.

Normally, to increase the end hardness of curable materials, the filler content of the materials or the functionability level of reactive monomers is increased or the chain length for the reactive monomers is decreased.

Polymerisable compositions which have a high filler content and are suitable as dental materials are described for example in The International Encyclopaedia of Composites (S. M. Lee, Ed., Vol. 2, VCH Publishers, New York 1990, page 182) and by L. Ehrnford (Swed. Dent. J. Suppl. 18, 1983). Highly-filled materials are known from EP-A-0 480 472, which can only be processed however when acted on by ultrasonic transmissions.

Furthermore, short-chain vinyl end-stopped polydimethyl siloxanes of the general formula:

$$CH_2=CH-R_2SiO-(SiR_2O)_n-SiR_2-CH=CH_2$$

are know from DE-A-2 646 726 where R is the same or different univalent, optionally substituted hydrocarbon radical free from aliphatic multiple bonds and n is 0 or an integer from 1 to 6. These compounds are used as inhibitors to regulate the cross-linking speed of addition cross-linked silicon impression materials.

DE-A-4 122 310 discloses on the other hand that compounds of the same general formula in which however n is an integer between 10 and 20 have no inhibitory effect whatsoever, but rather can be used to increase the end hardness of the cross-linked rubbers.

Thus it emerges from these documents that at least 22 chain links (i.e., wherein n is greater than or equal to 20 in the above mentioned general formula) must lie between two terminal C—C double bonds in molecules of the general formula stated in order to increase the hardness of the rubber; smaller intervals between the C—C double bonds inhibit cross-linking. This circumstance is also known from DE-A-4 324 685 in which diallyl maleinate and 1,3-divinyl-1,1,3,3-tetramethyldisiloxane can be named as examples of polymerization inhibitors, among others. Similarly, such molecules with more than 42 chain links (i.e., wherein n is greater than 40 in the above-mentioned formula) between the terminal double bonds are not imputed with any cross-linking properties.

There is a high demand for cross-linking monomers which increase the end hardness of a curable material but do not adversely affect the remaining properties, in particular the viscosity of the material.

The object of the present invention is to provide curable materials with increased end hardness and a viscosity suitable for processing in the dental field.

The object is achieved by a curable material containing:
(A) optionally organopolysiloxanes with at least two unsaturated groups in the molecule,
(B) organohydrogenpolysiloxanes with at least 3 SiH groups in the molecule,
(C) optionally organopolysiloxanes without reactive groups;
(D) catalyst
(E) optionally hydrophilizing agents,
(F) fillers and
(G) optionally standard dental additives, adjuvants and colorants,
characterized in that they additionally
(H) contain at least one silane dendrimer with terminal alkenyl groups.

Surprisingly, it has been ascertained that adding silane dendrimers to curable materials increases the end hardness of these materials considerably, but simultaneously acts against the increase in viscosity of the non-cured materials, although the silane dendrimers, at least in the first generation, have a considerably smaller double-bond interval as is regarded as strictly necessary in the prior art in order to have no inhibitory effect. Furthermore, with neighbouring double bonds, there is always the danger of complexing the catalyst, and thus an inhibitory effect is also to be observed. Successful polymerization using the silane dendrimers according to the invention is thus all the more astonishing.

Diorganopolysiloxanes with terminal triorganosiloxy groups of which at least one of the three organic groups is a vinyl group are preferred as component (A) Preferred diorganosiloxanes of this structure are represented by the following formula:

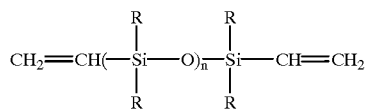

in which R represents a non-substituted or substituted monovalent hydrocarbon group with 1 to 6 C atoms, which is preferably free from aliphatic multiple bonds and n is chosen so that the viscosity lies between 4 and 50,000 mPas. At least 50% of the R radicals preferably consist of methyl groups, and examples for other R groups are ethyl, vinyl and 3,3,3-trifluoropropyl groups. Such molecules are described in U.S. Pat. No. 4,035,453, the disclosure of which should be included here. Component (A) is prepared according to standard procedures which are portrayed e.g. in W. Noll, "Chemie und Technologie der Silikone", Verlag Chemie Weinheim 2. edition 1964, pages 162–206 or J. Burghardt, Chemie und Technologie der Polysiloxane in "Silikone, Chemie und Technologie", Vulkan Verlag, Essen, 1989, pages 23–37.

Linear polydimethylsiloxanes of the above structure with the specified viscosity ranges for which the end groups consist of dimethylvinylsiloxy units and the other R substituents in the chain consist of methyl groups are particularly preferred.

Component (B) is preferably an organopolysiloxane with at least 3 Si-bonded hydrogen atoms per molecule. This organopolysiloxane preferably contains 0.01 to 1.7 wt.-% silicon-bonded hydrogens. The silicon valencies which are not saturated with hydrogen or oxygen atoms are saturated with monovalent hydrocarbon radicals which are free from aliphatic multiple bonds. The hydrocarbon radicals can be substituted or non-substituted. At least 50%, preferably 100% of the hydrocarbon radicals which are bonded to silicon atoms consist of methyl radicals. Such components are also described in the literature mentioned above with regard to structure and preparation.

The quantity ratios of components (A), (B) and (H) are preferably chosen so that 0.5 to 10 mol SiH units of component (B) is present per mol of unsaturated double bond of components (A) and (H). The sum of the components (A), (H), and the component (B) are in the range from 5 to 70 wt.-% relative to the total weight of all components. Preferably, they are in the range from 10 to 60 wt.-% and particularly in a range from 15 to 50 wt.-%.

Suitable components (C) are polymer organosiloxanes without reactive substituents as are described e.g. in W. Noll "Chemie and Technologie der Silikone", Verlag Chemie Weinheim, 1968, pages 212 ff. These are preferably linear, branched or cyclical organopolysiloxanes for which all silicon atoms are surrounded by oxygen atoms or monovalent hydrocarbon radicals, the hydrocarbon radicals being able to be substituted or non-substituted. The hydrocarbon radicals can be methyl, ethyl, $C_2$–$C_{10}$ aliphatics, trifluoropropyl groups as well as aromatic $C_6$–$C_{12}$ substituents. The component (C) contributes only to thinning and expanding the rubber network and acts as a plasticizer for the cured material. As it is a relatively cheap component, it contributes to the reduction of the preparation costs of the dental materials according to the invention.

Polydimethylsiloxanes which have trimethylsiloxy end groups are particularly preferred as component (C). The quantity of component (C) is 0 to 40 wt.-%, preferably 0 to 20 wt.-%, particularly preferably 0.1 to 10 wt.-%.

Component (D) is preferably a platinum complex which was prepared from hexachloroplatinum acid by reduction with tetramethyldivinyldisiloxane. These compounds are known per se. Other platinum compounds which accelerate addition cross-linking are also suitable. Platinum-siloxane complexes as described, e.g. in U.S. Pat Nos. 3,715,334, 3,775,352 and 3,814,730 are suitable, for example. The platinum catalyst is preferably used in quantities of 0.00005 to 0.05 wt.-%, particularly 0.0002 to 0.04 wt.-%, each calculated as elemental platinum and related to the overall weight of the material present with the components (A) to (H). To control the reactivity, it may be necessary to add an inhibitor which prevents premature cross-linking to elastomers. Such inhibitors are known and described, e.g. in U.S. Pat No. 3,933,880. Examples of this are acetylenic unsaturated alcohols such as 3-methyl-1-butyne-3-ol, 1-ethynylcyclohexane-1-ol, 3,5-dimethyl-1-hexyne-3-ol and 3-methyl-1-pentyne-3-ol. Examples of inhibitors based on vinyl siloxane are 1,1,3,3-tetramethyl-1,3-divinyl siloxane and poly-, oligo- and disiloxanes containing vinyl groups.

Component (E) is a hydrophilic character-giving agent or hydrophilizing agent which reduces the wetting angle of a drop of water or watery composition (e.g. plaster suspension, etc.) compared with the silicon composition and thus promotes a better wettability of the overall composition in the damp mouth region and thus a better flow-on behaviour of the pastes. The measurement of the wetting angle to determine the hydrophilicity of impression materials is e.g. described in DE-A-43 06 997, page 5, reference being made to this. The hydrophilizing agents are preferably not provided with reactive groups so that they are not incorporated into the polysiloxane network. Suitable hydrophilizing agents are preferably non-incorporable wetting agents from the group of hydrophilic silicone oils which are described in WO 87/03001 and in EP-B-0 231 420, the disclosure of which is to be taken into account in this respect. Furthermore, the ethoxylized fatty alcohols which are described in EP-B-0 480 238 are preferred. Furthermore, preferred hydrophilizing agents are the polyether carbosilanes known from WO 96/08230. Preferred are also the non-ionic perfluoralkylated surface-active substances described in WO 87/03001. Also preferred are the non-ionic surface-active substances which are described in EP-B-0 268 347, i.e. the nonylphenolethoxylates, polyethylene glycol-mono- und diesters, sorbitan esters as well as polyethylene glycol-mono- and diethers listed therein. The amounts of hydrophilizing agents used are 0 to 10 wt.-% relative to the overall weight of all components, preferably 0 to 2 wt.-% and particularly preferably 0.2 to 1 wt.-%. The wetting angle of a drop of water on the surface of a cured material according to the invention measured after 3 minutes, is preferably less than 60°, particularly preferably <50°, in particular <40°.

Among the fillers which can be used according to component (F) are non-reinforcing fillers such as quarz, cristobalite, calcium silicate, diatomaceous earth, zirconium silicate, montmorillonite such as bentonite, zeolite, including molecular sieves such as sodium aluminium silicate, metal oxide powder such as aluminium or zinc oxide or their mixed oxides, barium sulphate, calcium carbonate, plaster, glass and plastic powder. Among possible fillers are also reinforcing fillers such as e.g. pyrogenic or precipitated silicic acid and silica taluminium mixed oxide. The fillers named can be hydrophobized, for example by treatment with organosilanes or siloxanes or by the etherification of hydroxyl groups to alkoxy groups. One type of filler or also a mixture of at least two fillers can be used. The particle distribution is preferably chosen so that there are no fillers with particle sizes >50 $\mu$m. The overall content of fillers (F) is in the range from 10 to 90%, preferably 30 to 80%.

A combination of reinforcing and non-reinforcing fillers is particularly preferred. In this respect, the reinforcing fillers are in quantity ranges from 1 to 10 wt.-%, in particular 2 to 5 wt.-%. The difference in the named overall ranges, i.e. 9 to 70 wt.-%, in particular 28 to 55 wt.-% is comprised by the non-reinforcing fillers.

Pyrogenically-prepared high-dispersing silicic acids which have preferably been hydrophobized by surface-treatment are preferred as reinforcing fillers. The surface treatment can be carried out, for example with dimethyldichlorosilane, hexamethyldisilasane, tetramethylcyclotetrasiloxane or polymethylsiloxane.

Particularly preferred non-reinforcing fillers are quarzes, cristobalites and sodium aluminium silicates which can be surface-treated. The surface treatment can be largely carried out with the same methods as described in the case of the strengthening fillers.

Furthermore, the dental materials according to the invention can optionally contain additives such as plasticizers, pigments, anti-oxidizing agents, release agents, among others, as component (G). Similarly, for example, finely-distributed palladium or platinum can be contained as a hydrogen absorber. The metals can also be deposited on carrier materials. The materials according to the invention contain these kind of additives in quantities of preferably 0 to 2 wt.-%, particularly preferably 0 to 1 wt.-%.

The component (H) consists of silane dendrimers. Generally, three-dimensional, highly-ordered oligomer and polymer compounds are described as dendrimers, which are synthesized starting from small core molecules by a constantly repeating sequence of reactions. Monomer or polymer molecules with at least one reactive site are suitable as a core molecule. This is converted in a uni- or multi-level reaction with a reactant which accumulates at the reactive site of the core molecule and for its part has two new reactive sites. The conversion of core molecule and reactant yields the core cell (generation zero). By repeating the reaction, the reactive sites in the first reactant layer are converted with further reactants, again at least two new branching sites being introduced into the molecule each time (1$^{st}$ generation). The progressive branching leads to a geometrical growth of the number of atoms for each generation. As the overall size can only grow linearly because of the number of possible covalent bonds specified by the reactants, the molecules become more tightly packed from generation to generation and they change their shape from starfish-shaped to spherical.

Dendrimers of the zero and each further generation can be dendrimers used as component (H) according to the invention. Preferred are those of the zero and first generation although those of much higher generations can be used.

The dendrimers of the zero generation correspond to the general formula:

$$SiR_nR'_{4-n}$$

in which:

R is an alkenyl group with 2 to 5 C atoms, the C—C double bond being terminal, preferably a vinyl or allyl group, n is an integer from 1 and 4, preferably=4 and R' is a branched or unbranched aliphatic or aromatic hydrocarbon with 1 to 10 C atoms or hydrogen, preferably methyl or phenyl.

Dendrimers of other generations are obtained as a core molecule by conversion of tri- or tetraalkenyl silanes (preferably allyl and vinyl) in a first step with hydrogen-chloro-silanes. These products are converted in a further step with alkenyl-Grignard compounds.

Particularly preferred in this case are dendrimers of the first generation of the following formula:

$$SiR'_x((CH_2)_n—Si—((CH_2)_m—CH=CH_3)_3)_{4-x}$$

in which:

R' is defined as above, n=2, 3, 4 or 5, m=0, 1, 2 or 3, and x=0 or 1.

Particularly preferred dendrimers according to this general formula are:

Me—Si((CH$_2$—CH$_2$—Si(vinyl)$_3$)$_3$

Si((CH$_2$—CH$_2$—Si(vinyl)$_3$)$_4$

Me—Si((CH$_2$—CH$_2$—CH$_2$—Si(allyl)$_3$)$_3$

Si((CH$_2$—CH$_2$—CH$_2$—Si(allyl)$_3$)$_4$

Me—Si((CH$_2$—CH$_2$—Si(allyl)$_3$)$_3$

Si((CH$_2$—CH$_2$—Si(allyl)$_3$)$_4$

Me—Si((CH$_2$—CH$_2$—CH$_2$—Si(vinyl)$_3$)$_3$

Si((CH$_2$—CH$_3$—CH$_2$—Si(vinyl)$_3$)$_4$

A. W. van der Made and P. W. N. M. van Leeuwen describe the main synthesis of these silane dendrimers in J. Chem. Soc. Commen. (1992), page 1400 and in Adv. Mater. (1993), 5, no. 6, pages 366 ff. The synthesis begins for example with complete allylation of tetrachlorosilane to tetraallylsilane using 10% excess of allyl magnesium bromide in diethyl ether. In addition, the allyl groups are hydrosilylized with trichlorosilane in the presence of a platinum catalyst. Finally, the conversion takes place with allyl magnesium bromide in diethyl ether. As a result, a dendrimer is obtained with 12 allyl end groups. This first generation can also be converted to a second generation, 36 allyl groups being obtained. The same topic is also dealt with by D. Seyferth and D. Y. Son in Organometallics (1994), 13, 2682–2690.

Conversion products of tri- or tetra- or penta- or hexa- or hepta- or octaalkenyl(cyclo)siloxanes with hydrogen-chloro-silanes are furthermore possible as a core molecule. These are converted in a further step with alkenyl-Grignard compounds and lead to dendrimers with cyclical or linear siloxane cores which correspond to the following general formulae:

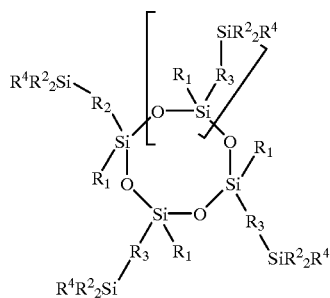

in which:

n=0, 1, 2, 3, 4 or 5,

R$^1$ is a saturated alkyl radical with 1 to 6 C atoms or hydrogen,

R$^2$ is an alkenyl group with 2 to 6 C atoms, the C—C double bond being present terminally, preferably a vinyl or allyl group, R$^3$ is an alkylene group with 2 to 6 C atoms and R$^4$ is either R$^2$ or —O—SiMe$_2$-allyl or —O—SiMe$_2$-vinyl.

Cyclical representatives with n=0 or 1, R$^1$=CH$_3$ and R$^2$=allyl or vinyl are preferred here.

Dendrimers of higher generations than expressed by the above formulae are also suitable.

Both purified tri-, tetra-, penta-, hexa-, hepta- or octasiloxane dendrimers as well as any mixtures of these dendrimers can be used according to the invention.

Silane dendrimers, the preparation and use as varnishes of which are known from DE-A-196 03 242 and 195 17 838 as well as from EP-A-0 743 313. Dendrimers listed there are also suitable for the purpose according to the invention.

Polyfunctional alkenyl compounds are furthermore suitable as cores. Particularly suitable are trimethylolpropanetriallylether, tetrallylpentaerythrite, Santolink XI-100 (Monsanto), tetraallyloxyethane, 1,3,5-benzoltricarbonic acid triallyl ester, 1,2,4-benzoltricarbonic acid triallylester, 1,2,4,5-benzoltetracarbonic acid tetrallylester, triallyl phosphate, triallyl citrate, triallyl isocyanurate, triallyloxytriazine, hexallylinosite, as well as in general compounds which possess at least two ethylenically unsaturated groups which can be optionally substituted, for example O-allyl, N-allyl, O-vinyl, N-vinyl, p-vinylphenolether groups. Possible polyenes are also described in U.S. Pat No. 3,661,744 and EP-A-0 188 880. The polyene can have e.g. the following structure: (Y)—

$(X)_m$, m being an integer greater than or equal to 2, preferably 2, 3 or 4, and X being chosen from the —[RCR]$_f$-CR═CRR, —O—CR═CR—R, —S—CR═CR—R, —NR—CR═CR—R group, f being an integer from 1 to 9 and the R radicals having the meanings H, F, Cl, furyl, thienyl, pyridyl, phenyl and substituted phenyl, benzyl and substituted benzyl, alkyl and substituted alkyl, alkoxy and substituted alkoxy as well as cycloalkyl and substituted cycloalkyl and each being able to be the same or different. (Y) is an at least difunctional organic radical which is constructed from atoms which are chosen from the C, O, N, Cl, Br, F, P, Si and H group.

The allyl- and/or vinyl esters of the at least difunctional carbonic acids are for example very suitable polyene compounds. Suitable carbonic acids for this are those with carbon chains of 2 to 20 C atoms, preferably 5 to 15 C atoms. Allyl or vinyl esters of aromatic dicarbonic acids such as phthalic acid or trimellithic acid are also very suitable. Allyl ethers of polyfunctional alcohols, preferably at least trifunctional alcohols are also suitable. Allyl ethers of trimethyl propane, pentaerythrite triallyl ether or 2,2-bis-oxyphenylpropane-bis-(diallyl phosphate) can be named as examples. Compounds of the cyanuric acid triallylester, triallyl triazintrione type and similar are also very suitable.

As the dendrimers to be used according to the invention are already terminated with C—C double bonds, the component (A) can be dispensed with or also contained to a high proportion. According to the desired properties of the dental materials, the component (H) is present in quantities from 0.1 to 50 wt.-%, preferably 0.1 to 20 wt.-%. Even the smallest additions effect a considerable increase in the end hardness of impression materials.

The materials are prepared by mixing the components (A) to (H) and curing in an addition reaction designated as hydrosilylizing in which, under the influence of the platinum catalyst (D), the SiH groups of the component (B) are added to the unsaturated groups of the components (A) and (H) respectively. For reasons of storage stability, it is preferable to formulate the materials in a two-component dosage form in which the overall component (B) is present in a so-called base paste. The overall component (D) is present physically separated from this in a so-called catalyst paste. The components (A) or (H) can be either present in the catalyst or base paste respectively, preferably a part of each of components (A) and (H) respectively being present in the base paste and a part of components (A) or (H) in the catalyst paste. The components (C), (E), (F) and (G) can be present in their full amount in the catalyst or base paste, it being preferable that a part each of the respective components are present in the catalyst paste and a part in the base paste.

The volume ratios of catalyst and base pastes can be 10:1 to 1:10. Particularly preferred volume ratios of base paste-:catalyst paste are 1:1 and 5:1 (5 parts base paste:1 part catalyst paste). In the case of a volume ratio of 1:1, the components (A) to (H) can be distributed as follows on base and catalyst paste.

TABLE 1

| Component | Base paste (wt.-%) | Catalyst paste (wt.-%) | Total in base and catalyst paste (wt.-%) |
| --- | --- | --- | --- |
| (A) | 0–60 | 0–60 | 0–60 |
| (B) | 2–60 | — | 1–30 |
| (C) | 0–20 | 0–20 | 0–20 |
| (D) | — | 0.0001–0.1 | 0.00005–0.05 |

TABLE 1-continued

| Component | Base paste (wt.-%) | Catalyst paste (wt.-%) | Total in base and catalyst paste (wt.-%) |
| --- | --- | --- | --- |
| (E) | 0–10 | 0–10 | 0–10 |
| (F) | 10–90 | 10–90 | 10–90 |
| (G) | 0–4 | 0–4 | 0–2 |
| (H) | 0–50 | 0–50 | 0.1–50 |

In the case of a volume ratio of 5 parts base paste to 1 part catalyst paste, preferred quantity ratios can be used as follows:

TABLE 2

| Component | Base paste (wt.-%) | Catalyst paste (wt.-%) | Total in base and catalyst paste (wt.-%) |
| --- | --- | --- | --- |
| (A) | 0–60 | 0–60 | 0–60 |
| (B) | 1.2–36 | — | 1–30 |
| (C) | 0–24 | 0–20 | 0–20 |
| (D) | — | 0.00025–0.25 | 0.00005–0.05 |
| (E) | 0–10 | 0–10 | 0–10 |
| (F) | 10–90 | 5–90 | 10–90 |
| (G) | 0–2.4 | 0–4 | 0–2 |
| (H) | 0–50 | 0–50 | 0.1–50 |

With a volume ratio 5:1, both pastes can be filled into tubular film bags and later, shortly before use, can be mixed using the mixing and dosing device PENTAMIX® (ESPE).

A dosage in the form of double-chambered cartridges or capsules is also possible.

The materials are particularly suitable as dental materials and are characterized by an unusually good end hardness of preferably shore hardness A≧80, preferably ≧90, particularly preferably shore hardness D≧40 with excellent processing viscosity. In particular, materials for bite measurement, temporary and permanent filling materials, crown and bridge materials as well as cements and varnishes can be considered as dental materials.

EXAMPLES

Preparation Example

1. Chlorine Pre-stage 2 g tetravinyl silane and 5 drops Karstedt catalyst are charged into a 50 ml three-necked flask under nitrogen. At room temperature, 12.1 g trichlorosilane are added dropwise and then heated for 9 more hours to 60° C. Volatile components are distilled off in a vacuum. 10 g of a light yellow oil is obtained.

2. Allyl Compound 10 g of the chlorine pre-stage from stage 1 are charged into a 1 l three-necked flask equipped with a reflux condenser and dropping funnel under nitrogen. At room temperature, 800 ml of a solution of allyl magnesium bromide in diethyl ether (1 mol/l) is added dropwise, the reaction mixture thereby comes to boiling point, followed by heating for 36 more hours under reflux. The cooled-down mixture is poured in portions onto ice-cold saturated ammonium chloride solution, the product extracted with ether and dried over magnesium sulphate. After distilling off the solvent and column chromatography purification (silica gel, hexane/trichloro methane eluent 5:1), 2.3 g (29% of theoretical value) of a colourless allyl compound is obtained.

Application Example

Dental impression materials are for example formulated as two components in a ratio of 1:1 when platinum catalysts are used. Subsequently, the formulation of a base and a catalyst paste is given.

1. Base Paste 23 wt.-% vinyl siloxane having a viscosity of 200 mPa (component (A)), 3 wt. of a polydimethyl hydrogen siloxane having a viscosity of 30 mPa and an SiH content of 7.3 mMol/g (component (B)) and 1 wt.-% of a polydimethyl siloxane having a viscosity of 50 mPa (component (G)) are stirred for an hour under a vacuum. Subsequently, 72 wt.-% finely ground surface-treated quarz (component (F)) and 1 wt.-% dendrimer from preparation example 2 (component (H)) are kneaded together for an hour under a vacuum.

2. Catalyst Paste 28 wt.-% vinyl siloxane having a viscosity of 200 mPa and 1 wt.-% of a polydimethyl siloxanes having a viscosity of 50 mPa are stirred for an hour under a vacuum. After the addition of 70.5 wt.-% of finely ground quarz, which was not surface-treated, as well as 0.5 wt.-% platinum catalyst (1.3% platinum part in silicon oil, component (D)), is kneaded for one hour without vacuum.

3. Base Paste without Dendrimer 24 wt.-% vinyl siloxane of 200 mPa in total is used instead of 1 wt.-% dendrimer.

Measurement Results

Identical parts of base paste 1 or 3 and catalyst paste 2 are homogenously mixed on a mixing block using a spatula and the setting time as well as the shore hardness D (DIN 53505) are measured in the same way.

| Base paste | Setting at 23° C. (sec.) | Shore hardness D after 24 hrs |
|---|---|---|
| 1 | 35–75 | 41 |
| 3 | 30–70 | 35 |

The described effect according to the invention, the increase in the end hardness, can be clearly recognized. The measurable parameters of the shore hardness increases by 6 units if a silane dendrimer is used according to the invention.

What is claimed is:

1. A curable material comprising:
   (A) optionally organopolysiloxanes with at least two unsaturated groups in the molecule,
   (B) organohydrogenpolysiloxanes with at least 3 SiH groups in the molecule,
   (C) optionally organopolysiloxanes without reactive groups,
   (D) catalyst,
   (E) optionally hydrophilizing agents,
   (F) fillers, and
   (G) optionally conventional dental additives, adjuvants and colorants,
   wherein said material additionally comprises
   (H) at least one silane dendrimer with terminal alkenyl groups.

2. The material according to claim 1 comprising:
   5–70 wt.-% components (A)+(B)+(H),
   0–40 wt.-% component (C),
   0.00005–0.05 wt.-% component (D), calculated as elemental platinum and related to the overall weight of the material present with the compounds (A) to (H),
   0–10 wt.-% component (E),
   10–90 wt.-% component (F),
   0–2 wt.-% component (G), and
   0.1–50 wt.-% component (H).

3. The material according to claim 1 comprising:
   10–60 wt.-% components (A)+(B)+(H),
   0–20 wt.-% component (C),
   0.0002–0.04 wt.-% component (D), calculated as elemental platinum and related to the overall weight of the material present with the compounds (A) to (H),
   0–2 wt.-% component (E),
   30–80 wt.-% component (F),
   0–1 wt.-% component (G), and
   0.1–20 wt.-% component (H).

4. The material according to claim 1, wherein the quantity ratio of components (A)+(H) to component (B) are chosen so that 0.5 to 10 mol SiH groups of component (B) are present per mol of unsaturated double bond of components (A) and (H).

5. The material according to claim 1, wherein said material comprises a dendrimer of the following formula as component (H):

$SiR_nR'_{4-n}$ in which:
   R is an alkenyl group with 2 to 5 C atoms, the C—C double bond being terminally present, preferably a vinyl or allyl group,
   n is an integer from 1 to 4, and
   R' is a linear or branched aliphatic or aromatic hydrocarbon radical with 1 to 10 C atoms or hydrogen.

6. The material according to claim 1, wherein said material comprises a dendrimer of the following formula as component (H):

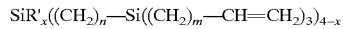

$SiR'_x((CH_2)_n-Si((CH_2)_m-CH=CH_2)_3)_{4-x}$ in which:
   R' is defined as in claim 5,
   n is 2, 3, 4 or 5,
   m is 0, 1, 2 or 3, and
   x is 0 or 1.

7. The material according to claim 6, wherein said material comprises at least one of the following dendrimers as component (H):

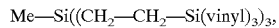

Me—Si((CH$_2$—CH$_2$—Si(vinyl)$_3$)$_3$,

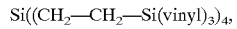

Si((CH$_2$—CH$_2$—Si(vinyl)$_3$)$_4$,

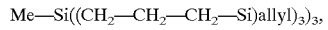

Me—Si((CH$_2$—CH$_2$—CH$_2$—Si)allyl)$_3$)$_3$,

Si—((CH$_2$—CH$_2$=—CH$_2$—Si(allyl)$_3$)$_4$,

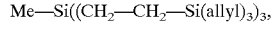

Me—Si((CH$_2$—CH$_2$—Si(allyl)$_3$)$_3$,

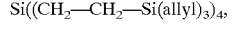

Si((CH$_2$—CH$_2$—Si(allyl)$_3$)$_4$,

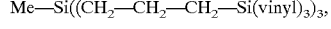

Me—Si((CH$_2$—CH$_2$—CH$_2$—Si(vinyl)$_3$)$_3$, or

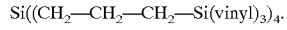

Si((CH$_2$—CH$_2$—CH$_2$—Si(vinyl)$_3$)$_4$.

8. The material according to claim 1, wherein said material comprises a dendrimer of the following formula as component (H):

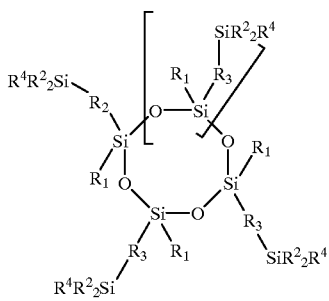

in which:

n is 0, 1, 2, 3, 4 or 5,

R' is a saturated alkyl radical with 1 to 6 C atoms or hydrogen, $R^2$ is an alkenyl group with 2 to 6 C atoms, the C—C double bond being terminally present, $R^3$ is an alkenyl group with 2 to 6 C atoms, and $R^4$ is either $R^2$ or —O—SiMe$_2$-allyl or —O—SiMe$_2$-vinyl.

9. The material according to claim 8, wherein n is 0

$R^1$ is CH$_3$, and $R^2$ is allyl or vinyl.

10. The material according to claim 1, wherein said material is present in the form of a base paste and a catalyst paste physically separated from it, the whole component (B) being present in the base paste and the whole component (D) being present in the catalyst paste and the remaining components being optionally distributed in the two pastes.

11. The material according to claim 10, wherein the volume ratio of base paste to catalyst paste is 10:1 to 1:10.

12. Use of a curable material containing the components (A) optionally organopolysiloxanes with at least two unsaturated groups in the molecule, (B) organohydrogenpolysiloxanes with at least 2 SiH groups in the molecule, (C) optionally organopolysiloxanes without reactive groups (D) catalyst (E) optionally hydrophilizing agents, (F) fillers (G) optionally other conventional additives, adjuvants and colorants, and (H) at least one silane dendrimer with terminal alkenyl groups as dental material, in particular as materials for bite registration, temporary or permanent filling materials, crown and bridging materials as well as cements and enamel.

13. The material of claim 5, wherein $R^1$ is methyl or phenyl.

14. The material according to claim 10, wherein the volume ratio of base paste to catalyst paste is 1:1 to 5:1.

15. The material according to claim 10, wherein the volume ratio of base paste to catalyst paste is 1;1 to 5;1.

* * * * *